(12) United States Patent
Davies et al.

(10) Patent No.: US 8,597,240 B2
(45) Date of Patent: Dec. 3, 2013

(54) COAXIAL CATHETER SHAFT HAVING BALLOON ATTACHMENT FEATURE WITH AXIAL FLUID PATH

(75) Inventors: William F. Davies, Athens, TX (US); Lanny R. Pepper, Larue, TX (US)

(73) Assignee: FutureMatrix Interventional, Inc., Athens, TX (US)

( * ) Notice: Subject to any disclaimer, the term of this patent is extended or adjusted under 35 U.S.C. 154(b) by 20 days.

(21) Appl. No.: 13/365,069

(22) Filed: Feb. 2, 2012

(65) Prior Publication Data

US 2012/0203173 A1 Aug. 9, 2012

Related U.S. Application Data

(60) Provisional application No. 61/438,833, filed on Feb. 2, 2011.

(51) Int. Cl.
*A61M 29/00* (2006.01)

(52) U.S. Cl.
USPC ...................................... 604/96.01

(58) Field of Classification Search
USPC ...................... 604/96.01, 103, 523
See application file for complete search history.

(56) References Cited

U.S. PATENT DOCUMENTS

| | | |
|---|---|---|
| 1,596,284 A | 8/1926 | Malmgren |
| 2,043,083 A | 6/1936 | Wappler |
| 3,769,981 A | 11/1973 | McWhorter |
| 3,981,415 A | 9/1976 | Fowler et al. |
| 4,367,396 A | 1/1983 | Ravinsky |
| 4,482,516 A | 11/1984 | Bowman et al. |
| 4,572,186 A | 2/1986 | Gould et al. |
| 4,637,396 A | 1/1987 | Cook |
| 4,652,258 A | 3/1987 | Drach |
| 4,702,252 A | 10/1987 | Brooks |
| 4,704,130 A | 11/1987 | Gilding et al. |
| 4,706,670 A | 11/1987 | Andersen et al. |
| 4,748,982 A | 6/1988 | Horzewski et al. |
| 4,796,629 A | 1/1989 | Grayzel |
| 4,834,755 A | 5/1989 | Silvestrini et al. |
| 4,884,573 A | 12/1989 | Wijay et al. |
| 4,952,357 A | 8/1990 | Euteneuer |
| 4,983,167 A | 1/1991 | Sahota |
| 4,998,421 A | 3/1991 | Zafiroglu |
| 5,042,985 A | 8/1991 | Elliott et al. |

(Continued)

OTHER PUBLICATIONS

Nylon; Wikipedia, the free encyclopedia; Jun. 27, 2008; pp. 1-7; available at http://en.wikipedia.org/wiki/Nylon.

(Continued)

*Primary Examiner* — Nicholas Lucchesi
*Assistant Examiner* — Melissa A Snyder
(74) *Attorney, Agent, or Firm* — Howison & Arnott, L.L.P.

(57) ABSTRACT

A catheter shaft for a balloon dilation catheter to be utilized with a guidewire includes an outer tubular member having a bore, a proximal end and a distal end with a guidewire tubular member coaxially disposed within the bore such that the inner surface of the outer tubular member and the outer surface of the guidewire tubular member define an annular inflation/deflation lumen extending between the proximal end of the shaft and the distal end of the outer tubular member with a plurality of discrete, spaced apart legs extending radially outward from the guidewire tubular member that serve as a stop or stops preventing movement of the guidewire tubular member into the outer tubular member when the legs abut the distal end of the outer tubular member.

20 Claims, 11 Drawing Sheets

(56) References Cited

U.S. PATENT DOCUMENTS

| | | | |
|---|---|---|---|
| 5,046,497 A | 9/1991 | Millar |
| 5,061,273 A | 10/1991 | Yock |
| 5,078,727 A | 1/1992 | Hannam et al. |
| 5,108,415 A | 4/1992 | Pinchuk et al. |
| 5,112,304 A | 5/1992 | Barlow et al. |
| 5,116,360 A | 5/1992 | Pinchuk et al. |
| 5,171,297 A | 12/1992 | Barlow et al. |
| 5,201,706 A | 4/1993 | Noguchi et al. |
| 5,207,700 A | 5/1993 | Euteneuer |
| 5,264,260 A | 11/1993 | Saab |
| 5,270,086 A | 12/1993 | Hamlin |
| 5,290,306 A | 3/1994 | Trotta et al. |
| 5,295,960 A | 3/1994 | Aliahmad et al. |
| 5,304,340 A | 4/1994 | Downey |
| 5,306,245 A | 4/1994 | Heaven |
| 5,306,246 A | 4/1994 | Sahatjian et al. |
| 5,314,443 A | 5/1994 | Rudnick |
| 5,330,429 A | 7/1994 | Noguchi et al. |
| 5,338,299 A | 8/1994 | Barlow |
| 5,344,401 A | 9/1994 | Radisch et al. |
| 5,358,486 A | 10/1994 | Saab |
| 5,410,797 A | 5/1995 | Steinke et al. |
| 5,451,209 A | 9/1995 | Ainsworth et al. |
| 5,451,233 A | 9/1995 | Yock |
| 5,464,394 A | 11/1995 | Miller et al. |
| 5,470,314 A | 11/1995 | Walinsky |
| 5,477,886 A | 12/1995 | Van Beugen et al. |
| 5,478,320 A | 12/1995 | Trotta |
| 5,492,532 A | 2/1996 | Ryan et al. |
| 5,549,552 A | 8/1996 | Peters et al. |
| 5,549,556 A | 8/1996 | Ndondo-Lay et al. |
| 5,554,120 A | 9/1996 | Chen et al. |
| 5,575,771 A | 11/1996 | Walinsky |
| 5,587,125 A | 12/1996 | Roychowdhury |
| 5,599,576 A | 2/1997 | Opolski |
| 5,620,649 A | 4/1997 | Trotta |
| 5,647,848 A | 7/1997 | Jorgensen |
| 5,690,642 A | 11/1997 | Osborne et al. |
| 5,728,063 A | 3/1998 | Preissman et al. |
| 5,741,325 A | 4/1998 | Chaikof et al. |
| 5,752,934 A | 5/1998 | Campbell et al. |
| 5,755,690 A | 5/1998 | Saab |
| 5,759,172 A | 6/1998 | Weber et al. |
| 5,769,817 A | 6/1998 | Burgmeier |
| 5,772,681 A | 6/1998 | Leoni |
| 5,788,979 A | 8/1998 | Alt et al. |
| 5,797,877 A | 8/1998 | Hamilton et al. |
| 5,820,613 A | 10/1998 | Van Werven-Fransesen et al. |
| 5,868,779 A | 2/1999 | Ruiz |
| 5,879,369 A | 3/1999 | Ishida |
| 5,928,181 A | 7/1999 | Coleman et al. |
| 5,972,441 A | 10/1999 | Campbell et al. |
| 5,980,486 A | 11/1999 | Enger |
| 6,007,544 A | 12/1999 | Kim |
| 6,010,480 A | 1/2000 | Abele et al. |
| 6,012,457 A | 1/2000 | Lesh |
| 6,015,430 A | 1/2000 | Wall |
| 6,024,722 A | 2/2000 | Rau et al. |
| 6,024,740 A | 2/2000 | Lesh et al. |
| 6,027,779 A | 2/2000 | Campbell et al. |
| 6,036,697 A | 3/2000 | DiCaprio |
| 6,036,715 A | 3/2000 | Yock |
| 6,117,101 A | 9/2000 | Diederich et al. |
| 6,124,007 A | 9/2000 | Wang et al. |
| 6,127,597 A | 10/2000 | Beyar et al. |
| 6,129,708 A | 10/2000 | Enger |
| 6,156,254 A | 12/2000 | Andrews et al. |
| 6,159,238 A | 12/2000 | Killion et al. |
| 6,164,283 A | 12/2000 | Lesh |
| 6,171,297 B1 | 1/2001 | Pedersen et al. |
| 6,183,492 B1 | 2/2001 | Hart et al. |
| 6,186,978 B1 | 2/2001 | Samson et al. |
| 6,187,013 B1 | 2/2001 | Stollze et al. |
| 6,213,995 B1 | 4/2001 | Steen et al. |
| 6,234,995 B1 | 5/2001 | Peacock, III |
| 6,245,064 B1 | 6/2001 | Lesh et al. |
| 6,254,599 B1 | 7/2001 | Lesh et al. |
| 6,263,236 B1 | 7/2001 | Kasinkas et al. |
| 6,270,902 B1 | 8/2001 | Tedeschi et al. |
| 6,290,485 B1 | 9/2001 | Wang |
| 6,305,378 B1 | 10/2001 | Lesh |
| 6,306,154 B1 | 10/2001 | Hudson et al. |
| 6,309,379 B1 | 10/2001 | Willard et al. |
| 6,315,751 B1 | 11/2001 | Cosgrove et al. |
| 6,328,925 B1 | 12/2001 | Wang et al. |
| 6,361,529 B1 | 3/2002 | Goodin et al. |
| 6,394,995 B1 | 5/2002 | Solar et al. |
| 6,544,219 B2 | 4/2003 | Happ et al. |
| 6,626,889 B1 | 9/2003 | Simpson et al. |
| 6,663,648 B1 | 12/2003 | Trotta |
| 6,702,750 B2 | 3/2004 | Yock |
| 6,702,782 B2 | 3/2004 | Miller et al. |
| 6,706,051 B2 | 3/2004 | Hudson et al. |
| 6,733,487 B2 | 5/2004 | Keith et al. |
| 6,743,196 B2 | 6/2004 | Barbut et al. |
| 6,746,425 B1 | 6/2004 | Beckham |
| 6,755,845 B2 | 6/2004 | Kieturakis et al. |
| 6,761,708 B1 | 7/2004 | Chiu et al. |
| 6,899,713 B2 | 5/2005 | Shaolian et al. |
| 6,905,743 B1 | 6/2005 | Chen et al. |
| 6,911,038 B2 | 6/2005 | Mertens et al. |
| 6,942,680 B2 | 9/2005 | Grayzel et al. |
| 6,977,103 B2 | 12/2005 | Chen et al. |
| 7,252,650 B1 | 8/2007 | Andrews et al. |
| 7,300,415 B2 | 11/2007 | McMurtry et al. |
| 7,309,324 B2 | 12/2007 | Hayes et al. |
| 7,354,419 B2 | 4/2008 | Davies et al. |
| 7,435,254 B2 | 10/2008 | Chouinard et al. |
| 7,500,982 B2 | 3/2009 | Pepper |
| 7,544,201 B2 | 6/2009 | Pepper |
| 7,635,510 B2 | 12/2009 | Horn et al. |
| 7,662,163 B2 | 2/2010 | Grayzel et al. |
| 7,682,335 B2 | 3/2010 | Pepper et al. |
| 2002/0058960 A1 | 5/2002 | Hudson et al. |
| 2002/0077653 A1 | 6/2002 | Hudson et al. |
| 2002/0161388 A1 | 10/2002 | Samuels et al. |
| 2004/0015182 A1 | 1/2004 | Kieturakis et al. |
| 2004/0039332 A1 | 2/2004 | Kantor |
| 2004/0073163 A1 | 4/2004 | Tomaschko et al. |
| 2004/0073299 A1 | 4/2004 | Hudson et al. |
| 2004/0082965 A1 | 4/2004 | Beckham |
| 2004/0109964 A1 | 6/2004 | Beckham |
| 2004/0176740 A1 | 9/2004 | Chouinard |
| 2005/0027249 A1 | 2/2005 | Reifart et al. |
| 2005/0033225 A1 | 2/2005 | Wu et al. |
| 2005/0102020 A1 | 5/2005 | Grayzel et al. |
| 2005/0121073 A1 | 6/2005 | Carroll |
| 2005/0123702 A1 | 6/2005 | Beckham |
| 2005/0267408 A1 | 12/2005 | Grandt et al. |
| 2005/0271844 A1 | 12/2005 | Mapes et al. |
| 2006/0015133 A1 | 1/2006 | Grayzel et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2007/0010847 A1 | 1/2007 | Pepper |
| 2007/0059466 A1 | 3/2007 | Beckham |
| 2007/0093865 A1 | 4/2007 | Beckham |
| 2007/0213760 A1 | 9/2007 | Hayes et al. |
| 2007/0219490 A1 | 9/2007 | Pepper et al. |
| 2008/0009793 A1 | 1/2008 | Dabbs |
| 2008/0082050 A1 | 4/2008 | Solar et al. |
| 2008/0183132 A1 | 7/2008 | Davies et al. |
| 2008/0188805 A1 | 8/2008 | Davies et al. |
| 2008/0255507 A1* | 10/2008 | Mushtaha .................. 604/103 |
| 2009/0043254 A1 | 2/2009 | Pepper et al. |
| 2009/0171277 A1 | 7/2009 | Pepper |
| 2009/0247947 A1 | 10/2009 | Pepper |
| 2009/0294031 A1 | 12/2009 | Pepper et al. |

(56) References Cited

U.S. PATENT DOCUMENTS

OTHER PUBLICATIONS

Fiber; Wikipedia, the free encyclopedia; Jun. 27, 2008; pp. 1-3; available at http://en.wikipedia.org/wiki/Fiber.

Putnam Plastics Corporation; Putnam Plastics—Thermoset Polyimide Tubing; Mar. 20, 2005; available at www.putnamplastics.com.

Arkema Group; Pebax® Application Areas; Jun. 2000.

* cited by examiner

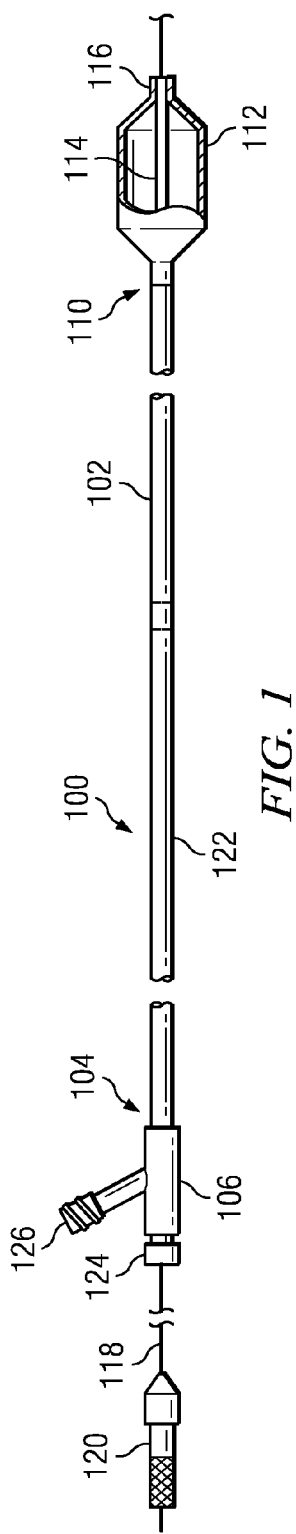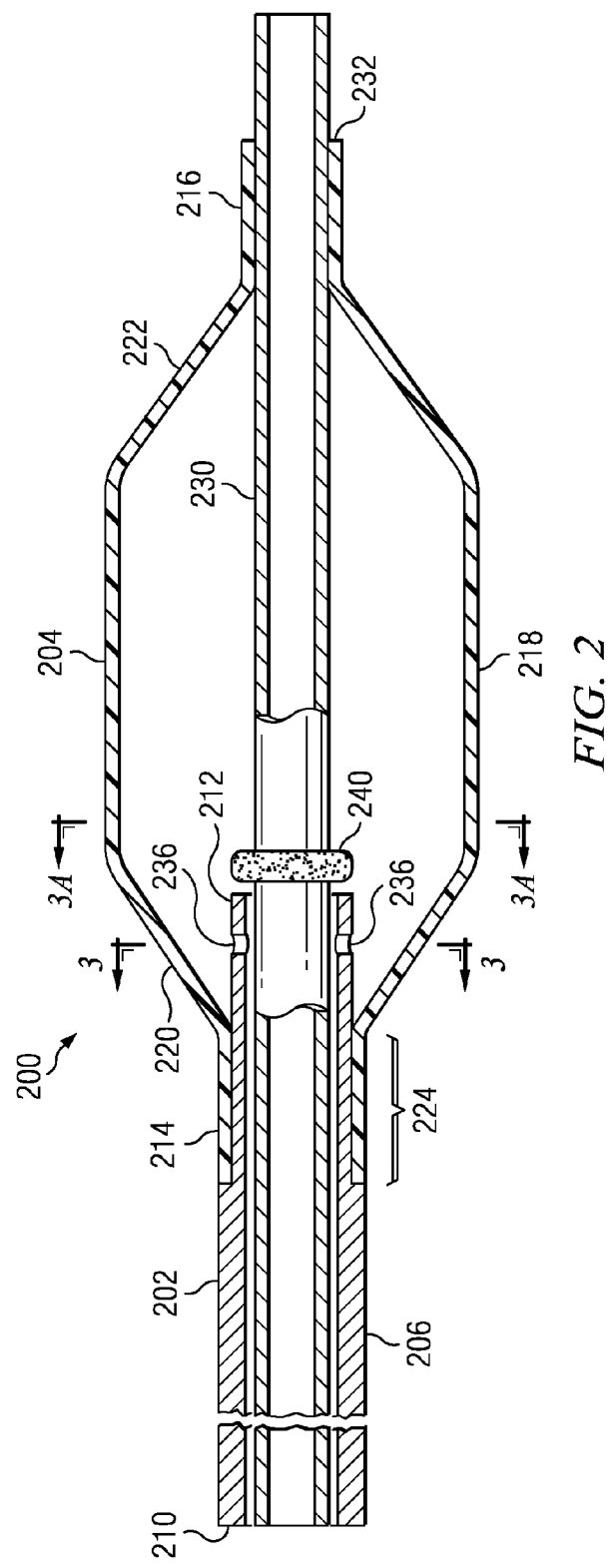
FIG. 1
FIG. 2 (PRIOR ART)

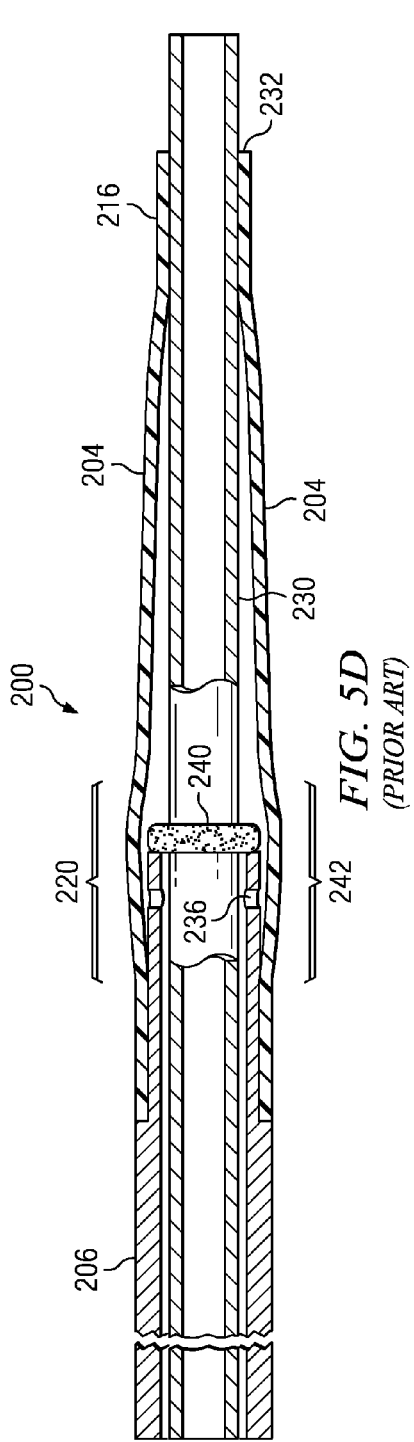
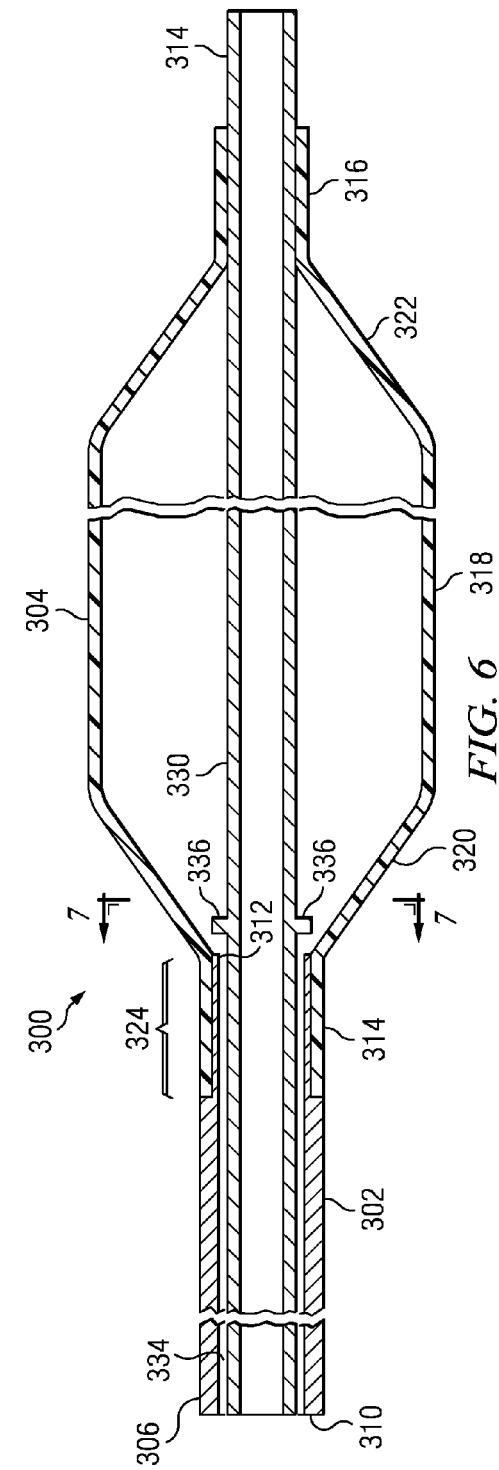
FIG. 5D (PRIOR ART)
FIG. 6

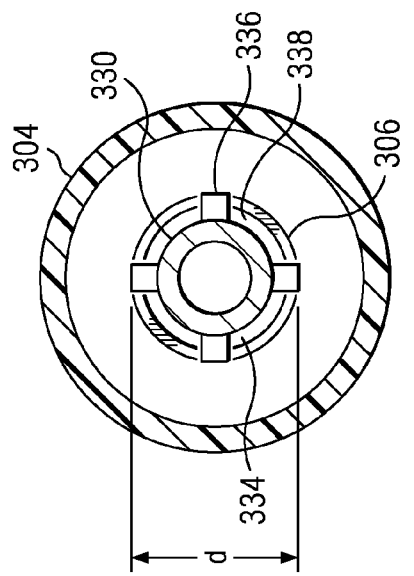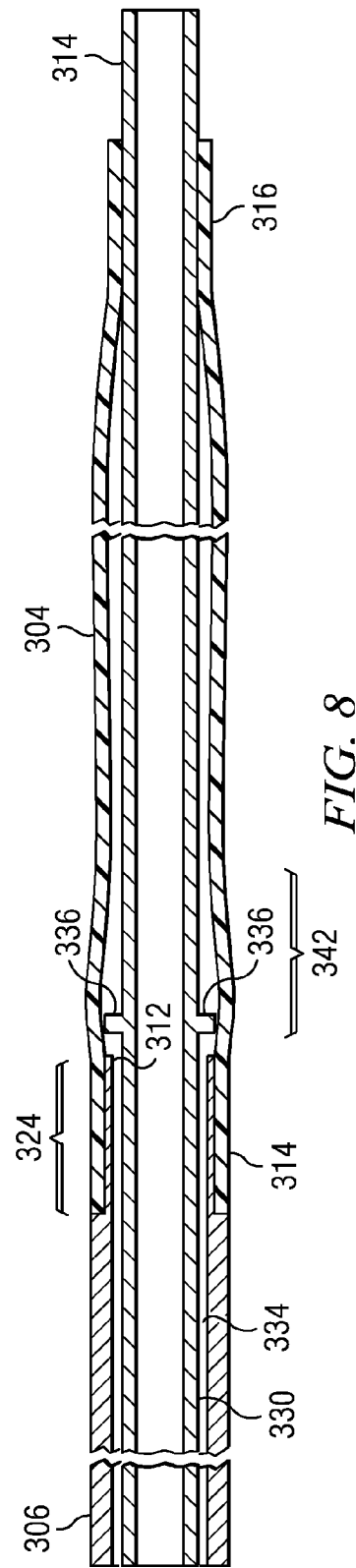

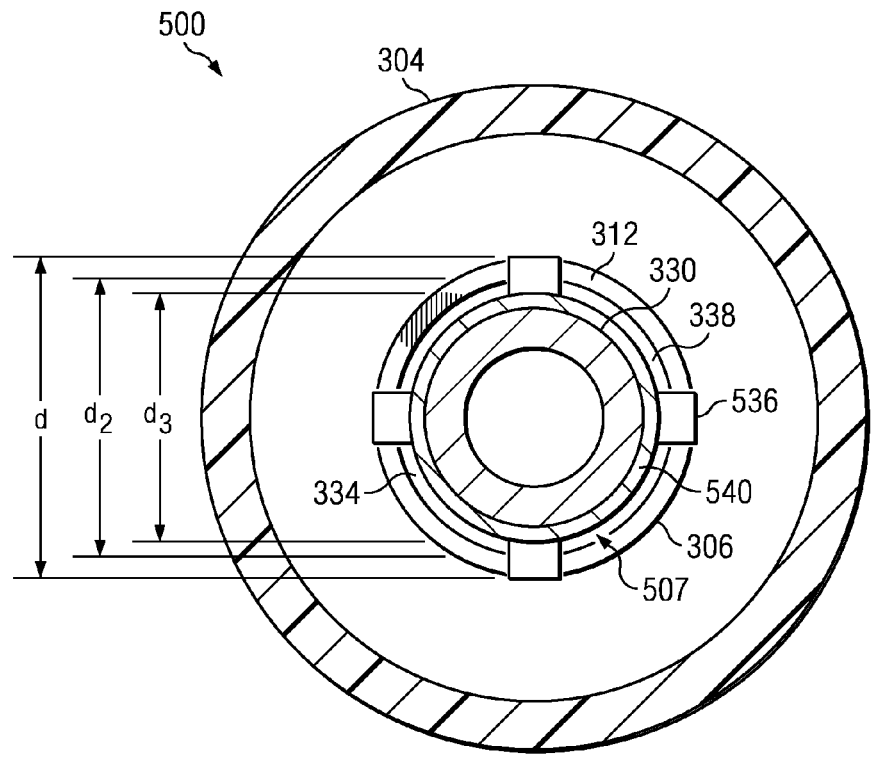
FIG. 11
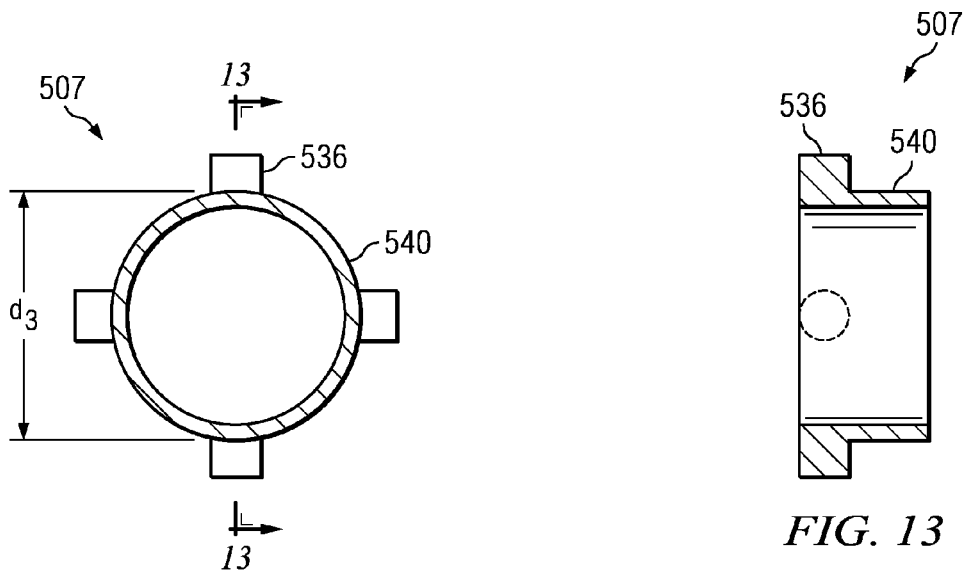
FIG. 12
FIG. 13

COAXIAL CATHETER SHAFT HAVING BALLOON ATTACHMENT FEATURE WITH AXIAL FLUID PATH

CROSS-REFERENCE TO RELATED APPLICATIONS

This application claims benefit of U.S. Provisional Application No. 61/438,833, filed on Feb. 2, 2011, and entitled COAXIAL CATHETER SHAFT HAVING BALLOON ATTACHMENT FEATURE WITH AXIAL FLUID PATH.

TECHNICAL FIELD

The current invention relates generally to catheters and shafts therefor, and more specifically to coaxial shafts for balloon dilation catheters. In particular, it relates to a coaxial catheter shaft having an improved stop for limiting relative movement between the shaft elements while simultaneously providing a means of rapidly deflating a dilation balloon attached to the shaft.

BACKGROUND

Treatment of various conditions using balloon dilation catheters, for example, so-called Percutaneous Transluminal Angioplasty Catheters (i.e., "PTACs"), has progressed into narrower and more remote vessels within the body. This progression has necessitated the use of catheters having correspondingly smaller shaft diameters and longer shaft lengths. The trend towards catheters with smaller diameter, longer shafts has introduced additional concerns. The inflation/deflation time performance (i.e., the time required for inflation and deflation of the balloon) has increased with the use of longer, smaller diameter catheters. Deflation time for a dilation balloon can be significant, especially when it is desired to move the catheter to different locations to expand different portions of a body lumen, for example, a blood vessel. Additionally, the operating pressure of dilation balloons continues to rise. At one time a balloon inflation pressure of 10 atmospheres was considered high. Now, dilation balloons with operating pressures of up to 30 atmospheres are known, and it is foreseeable that even higher pressures may be utilized in the near future.

One conventional design of balloon catheter shafts is the coaxial design, wherein two concentrically disposed tubular members form the catheter shaft. In coaxial catheter shafts, the inside of the inner tubular member is used for the guidewire lumen, while the outer tubular member is used for the catheter shaft body. A jacket may be positioned over the outer tubular member to provide desired surface properties. The annular space between the outer surface of the inner tubular member and the inner surface of the outer tubular member forms an inflation/deflation lumen for transporting saline solution, contrast media or other non-compressible fluid for inflating and deflating the balloon.

The coaxial shaft design is considered to maximize the cross-sectional area available for the inflation/deflation lumen, thereby providing the best inflation/deflation performance for a given length catheter. The incompressible fluid used to inflate the balloon may be introduced into the balloon through the annular space between the outer surface of the inner tubular member and the inner surface of the outer tubular member or through radial ports or holes formed in the distal end of the outer tubular member and positioned inside the balloon.

However, fluid flow in the vicinity of the interconnection between a dilation balloon and a coaxial catheter shaft may be problematic, especially during the deflation phase of a procedure. To deflate a dilation balloon, the incompressible fluid used to inflate the balloon must be withdrawn, in some cases under negative pressure to decrease the amount of time required to deflate the balloon. Since a dilation balloon is typically formed from a thin, flexible polymer, the balloon collapses unpredictably during the deflation process. The collapsed balloon may partially or completely block the annular space between the inner tubular member and the outer tubular member and/or the radial inflation ports formed in the outer tubular member before the balloon is fully deflated. Further, conventional coaxial catheter shaft designs require that the balloon be bonded to the outer tubular member with a portion of the outer tubular member (i.e., the portion with the radial inflation ports) extending into the balloon. The portion of the outer tubular member extending into the balloon increases the diameter of the balloon in its deflated configuration, which in turn, requires the use of a larger introducer to insert the balloon into a body lumen.

Thus, there exists a need for a coaxial catheter shaft that provides for rapid deflation and for a reduced diameter of the balloon/catheter assembly in a deflated state.

SUMMARY

A catheter shaft for a balloon dilation catheter to be utilized with a guidewire has a proximal end and a distal end and includes an outer tubular member having a bore, a proximal end and a distal end. A guidewire tubular member is coaxially disposed within the bore of the outer tubular member along the length of the outer tubular member such that the inner surface of the outer tubular member and the outer surface of the guidewire tubular member define an annular inflation/deflation lumen extending between the proximal end of the shaft and the distal end of the outer tubular member. The proximal end of the shaft is adapted for connection to an access fitting having a first port for conveying a guidewire into the guidewire tubular member and a second port for conveying a fluid into the inflation/deflation lumen.

A plurality of discrete, spaced apart legs extend radially outward from the guidewire tubular member. At least one of the legs extends radially beyond the inside diameter of the outer tubular member such that the leg blocks movement of the guidewire tubular member into the outer tubular member when the leg of the guidewire tubular member abuts the distal end of the outer tubular member. A plurality of legs may be positioned at spaced apart circumferential positions around the exterior perimeter of the guidewire tubular member whereby the legs define a plurality of fluid passageways between the outer tubular member and the guidewire tubular member when the legs are abutted against the distal end of outer tubular member. The legs may be disposed at equally spaced circumferential positions around the circumference of the guidewire tubular member and extend radially outward therefrom. In one variation, the legs are formed from a thermoplastic material and may be affixed to the guidewire tubular member by thermal and/or compression welding.

The distal end of the outer tubular member is adapted for connection to a proximal neck portion of a dilation balloon, with a portion of the guidewire tubular member extending beyond the distal end of the outer tubular member. The portion of the guidewire tubular member extending beyond the distal end of the outer tubular member is adapted to pass through the interior of the dilation balloon for connection to the distal end of the balloon. The outer tubular member of the catheter shaft may include a reduced diameter distal portion adapted to receive the proximal neck portion of a dilation balloon with the proximal end of the proximal neck portion in abutting relation with the proximal end of the reduced diameter portion of the outer tubular member.

In another variation, a dilation catheter assembly includes a catheter shaft having a proximal end and a distal end. The shaft includes an outer tubular member having a bore, a proximal end and a distal end with a guidewire tubular member coaxially disposed within the bore of the outer tubular member along the length of the outer tubular member. The inner surface of the outer tubular member and the outer surface of the guidewire tubular member define an annular inflation/deflation lumen extending between the proximal end of the shaft and the distal end of the outer tubular member. A dilation balloon is connected to the distal end of the outer tubular member and to the guidewire tubular member. The dilation balloon including proximal and distal neck sections, a barrel section and proximal and distal cone sections disposed between the proximal and distal neck sections and the barrel section. The dilation balloon may be one of a compliant, semi-compliant or non-compliant balloon.

A plurality of legs extend from the guidewire tubular member distal from the distal end of the outer tubular member. The legs extend radially outward from the guidewire tubular member and beyond the inside diameter of the outer tubular member such that the legs block movement of the guidewire tubular member into the outer tubular member when the legs abut the distal end of the outer tubular member. When the legs are abutted against the distal end of the outer tubular member, the legs define a plurality of fluid passageways between the outer tubular member and the guidewire tubular member such that fluid may flow into and out of the annular inflation/deflation lumen. In one variation, the legs may be disposed at equally spaced circumferential positions around the circumference of the guidewire tubular member and extend radially outward therefrom.

In one aspect, the distal end of the outer tubular member is adapted for connection to a proximal neck portion of the dilation balloon. The portion of the guidewire tubular member extending beyond the distal end of the shaft is adapted to pass through the interior of the dilation balloon and to be connected to the distal end of the balloon. The outer tubular member may include a reduced diameter distal portion adapted to receive the proximal neck portion of the dilation balloon with the proximal end of the proximal neck portion of the balloon in abutting relation with the proximal end of the reduced diameter portion of the outer tubular member.

In another aspect, the guidewire tubular member is formed from a thermoplastic material and the legs are affixed to the guidewire tubular member by thermal welding at spaced apart intervals around the periphery of the guidewire tubular member. The legs may be affixed to the guidewire tubular member by ultrasonic, chemical or thermal compression welding.

The dilation catheter assembly may further include an access fitting affixed to the proximal end of the shaft, the access fitting including a first port allowing guidewire to pass into and out of the guidewire tubular member, and a second, inflation/deflation port in fluid communication with the annular inflation/deflation lumens.

BRIEF DESCRIPTION OF THE DRAWINGS

For a more complete understanding, reference is now made to the following description taken in conjunction with the accompanying drawings in which:

FIG. 1 is a side view, with portions broken away, of a balloon dilation catheter assembly in accordance with one embodiment of the disclosure;

FIG. 2 is a partial longitudinal cross-sectional view of a prior art balloon dilation catheter including a coaxial catheter shaft and a dilation balloon attached to the catheter shaft;

FIG. 5A illustrates the catheter assembly during inflation;

FIG. 5B illustrates the catheter assembly during the initial stage of deflation;

FIG. 5C illustrates the catheter assembly during the later stages of deflation;

FIG. 5D is a partial longitudinal sectional view of the dilation balloon catheter assembly of FIG. 2 in a deflated configuration;

FIG. 6 is a longitudinal sectional view of a catheter assembly including a coaxial shaft according to the disclosure;

FIG. 7 is a partial cross-sectional view of the catheter assembly and coaxial shaft of FIG. 6 taken along line 7-7 of FIG. 6;

FIG. 8 is a longitudinal sectional view of the catheter assembly and coaxial shaft of FIG. 7, in which the dilation balloon is in a deflated configuration;

FIG. 11 is a partial cross-sectional end view of the catheter assembly and coaxial shaft of FIG. 10 taken along line 11-11 of FIG. 10;

FIG. 12 is an end view of a leg assembly according to the disclosure; and

FIG. 13 is a side cross-sectional view of the leg assembly of FIG. 12 taken along line 13-13 of FIG. 12.

DETAILED DESCRIPTION

Figure 3:
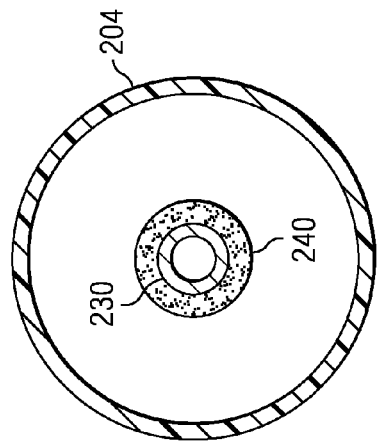
FIG. 3 is a cross-sectional end view of the prior art balloon dilation catheter of FIG. 2, taken along line 3-3 of FIG. 2.

Referring now to the drawings, wherein like reference numbers are used herein to designate like elements throughout, the various views and embodiments of a coaxial catheter shaft having balloon attachment feature with axial fluid path are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a balloon dilation catheter assembly 100 in accordance with one embodiment of the disclosure. The catheter assembly 100 includes a coaxial shaft 102 having a proximal end 104 that is configured for attachment to an access fitting 106. Shaft 102 includes a distal end 110 configured for attachment of a dilation balloon 112. The coaxial shaft 102 includes an inner tubular member 114 (also known as a guidewire tubular member) disposed within an outer tubular member 122. The guidewire tubular member 114 extends longitudinally through the catheter from the access fitting 106 to the distal end 116 of the balloon 112. Guidewire tubular member has a bore defining a guidewire lumen that allows a conventional guidewire 118 to be threaded through the interior of the catheter. A guidewire manipulator 120 may be secured to the guidewire 118 for rotating the guidewire from the proximal end of the catheter. Guidewire tubular member 114 is disposed within the outer tubular member 122. Outer tubular member 122 and guidewire tubular member 114 define an annular inflation/deflation lumen therebetween that conveys contrast liquid or other non-compressible inflation fluid through shaft 102 from access fitting 106 to dilation balloon 112, thereby allowing the balloon to be selectively inflated and deflated. Access fitting 106 may be of conventional design, having a first port 124 allowing guidewire 118 to pass into and out of the guidewire lumen, and a second, inflation/deflation port 126 in fluid communication with the annular inflation/deflation lumens.

FIG. 2 is a partial longitudinal sectional view of a prior art balloon dilation catheter 200 including a coaxial catheter shaft 202 and a dilation balloon 204 attached to the catheter shaft. The overall configuration of the catheter 200 is similar to that of the catheter 100 shown in FIG. 1, except for the differences in the shaft structure in the vicinity of the balloon attachment as further described herein. FIG. 2 illustrates dilation balloon 204 in an inflated configuration. Coaxial catheter shaft 202 includes an outer tubular member 206 having a proximal end 210 and a distal end 212. Dilation balloon 204 includes proximal and distal neck sections 214, 216, respectively, a barrel section 218 and proximal and distal cone sections 220, 222 disposed between the barrel section and the neck sections. Outer tubular member 206 includes a necked down or reduced diameter section 224 adjacent the distal end 212 of the outer tubular member. The proximal neck section 214 of dilation balloon 204 is fitted over and adhered to the outer tubular member 206 in the reduced diameter section 224 of the member. As illustrated, outer tubular member 206 extends into dilation balloon 204 through proximal neck section 214 and into proximal cone section 220.

Figure 3A:
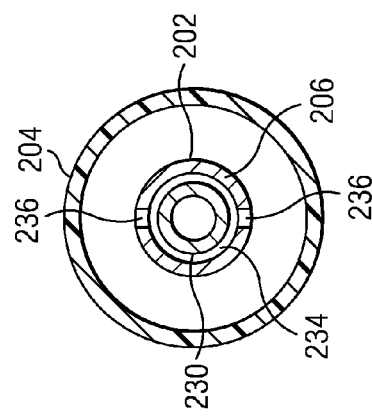
FIG. 3A is a another cross-sectional end view of the prior art balloon dilation catheter of FIG. 2, taken along line 3A-3A of FIG. 2.

FIG. 3 is a partial cross-sectional view of the prior art balloon dilation catheter 200 of FIG. 2 taken along line 3-3. FIG. 3A is a partial cross-sectional view of the prior art balloon dilation catheter 200 of FIG. 2 taken along line 3A-3A. Referring to FIGS. 2, 3 and 3A in conjunction, coaxial catheter shaft 202 includes a guidewire tubular member 230 disposed inside of outer tubular member 206 and extending from inflation/deflation port 126 (FIG. 1) to the distal end 232 of dilation balloon 204. The distal neck section 216 of dilation balloon 204 is adhered to guidewire tubular member 230 such that the balloon is advanced through a body lumen such as a blood vessel, as balloon dilation catheter 200 is inserted into the lumen.

Figure 4:
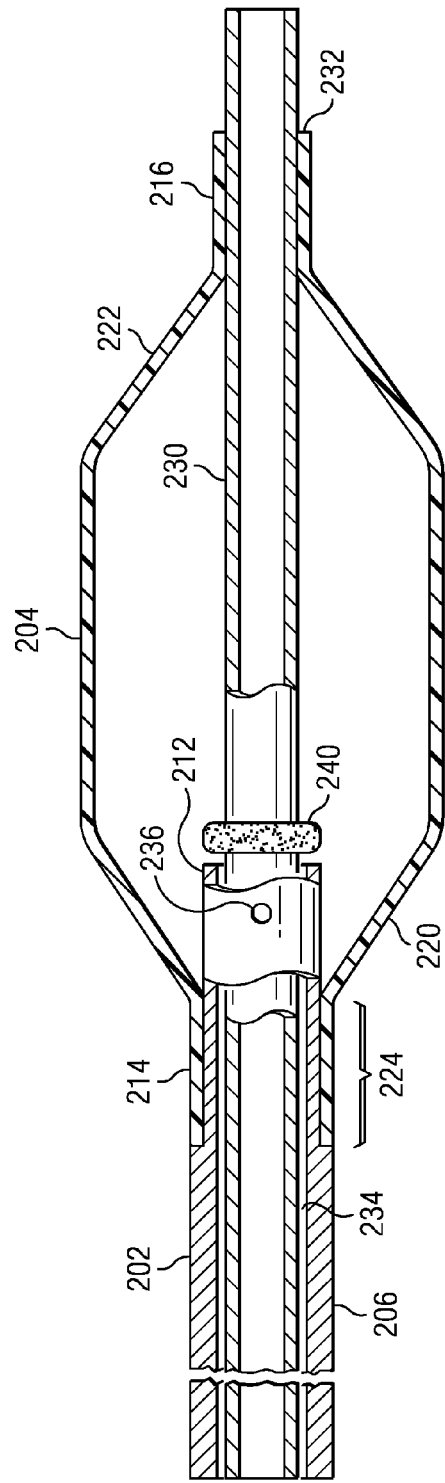
FIG. 4 is a partial cross-sectional and partial cutaway view of the prior art balloon dilation catheter assembly of FIG. 2, rotated ninety degrees from the view of FIG. 2.

FIG. 4 is a partial sectional and partial cutaway view of the prior art balloon dilation catheter assembly 200 of FIG. 2, rotated ninety degrees. As illustrated, the inner surface of the outer tubular member 206 and the outer surface of the guidewire tubular member 230 define an annular inflation/deflation lumen 234 (FIG. 3) extending from inflation/deflation port 126 (FIG. 1) and into dilation balloon 204. One or more radial holes or apertures 236 near or adjacent the distal end 212 of outer tubular member 206 provide fluid communication between annular inflation/deflation lumen 234 and the interior of dilation balloon 204, enabling inflation and deflation of the balloon through inflation/deflation port 126 and the annular inflation/deflation lumen.

Referring still to FIG. 4, an annular stop member 240 is disposed about the circumference of guidewire tubular member 230 near or adjacent to the distal end of outer tubular member 206. Stop member 240 may be separately formed and then glued or welded in place around the guidewire tubular member 230 or it may be formed in place from adhesive or plastic applied to the guidewire tubular member. It is typically disposed within the proximal cone region 220 of dilation balloon 204. Stop member 240 limits the rearward movement of the guidewire tubular member 230 relative to the outer tubular member 206. Without the stop member 204, rearward movement of the guidewire tubular member 230 would pull the distal neck section 216 of dilation balloon 204 toward the distal end 212 of the outer tubular member 206 and collapse the balloon in an accordion-like manner. Such an accordion-like collapse is undesirable in that the collapsed balloon will have a relatively large diameter, potentially impeding movement of the balloon within a body lumen such as a blood vessel.

Referring now to FIGS. 5A-5D, operation of the prior art catheter assembly 200 having a guidewire tubular member 230 with radial ports 236 and an annular stop member 240 is illustrated during inflation and deflation. As will be explained, while the configuration prevents an accordion-like collapse of dilation balloon 204, there are drawbacks to this prior art configuration.

Figure 5A:
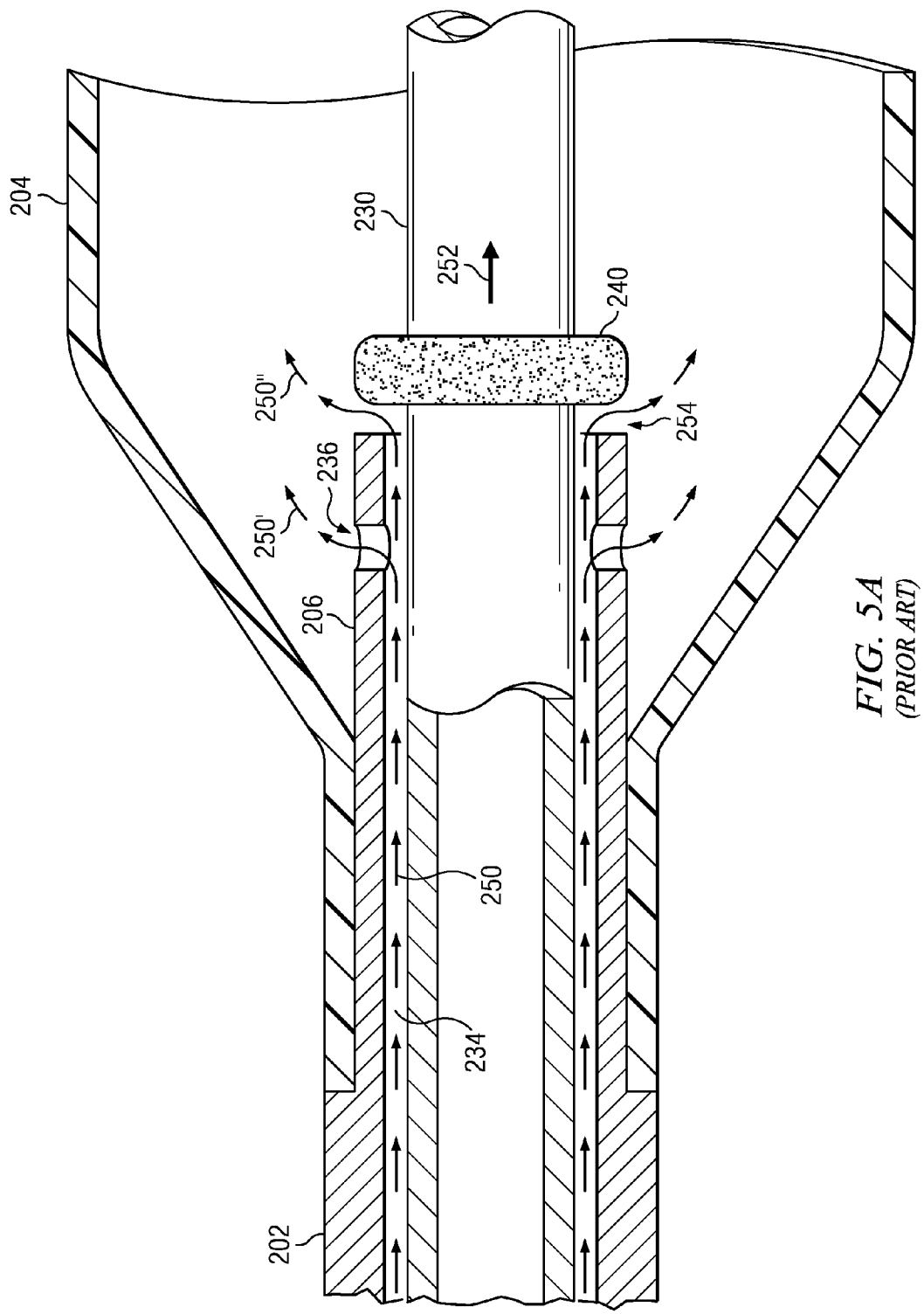
FIGS. 5A-5C are enlarged cross-sectional side views of the balloon attachment area of the prior art dilation balloon catheter of FIG. 2 at various stages of inflation/deflation, in particular.

FIG. 5A is an enlarged view of the balloon attachment area of the coaxial catheter shaft 202 during inflation of the balloon 204. Incoming fluid (denoted by arrows 250) is introduced into the proximal end of the catheter shaft and forced under pressure through the annular space 234 between the guidewire tubular member 230 and the outer tubular member 206. The pressurized fluid 250 flows (denoted by arrows 250') through the radial ports 236 from the annular space 234 into the interior of the balloon 204, thus inflating the balloon. The pressurized fluid 250 in the annular space 234 also urges the annular stop 240 and the guidewire tubular member 230 in the distal direction (denoted by arrow 252). If the incoming fluid pressure is great enough, the annular stop 240 may move away from the end of the outer tubular member 206, thereby creating a temporary annular passage 254 through which the pressurized fluid 250 may also flow (denoted by arrows 250"). Because the area of the temporary annular passage 254 may be much greater than the area of the radial ports 236, flow through the temporary annular passage may greatly speed inflation of the balloon 204.

Figure 5B:
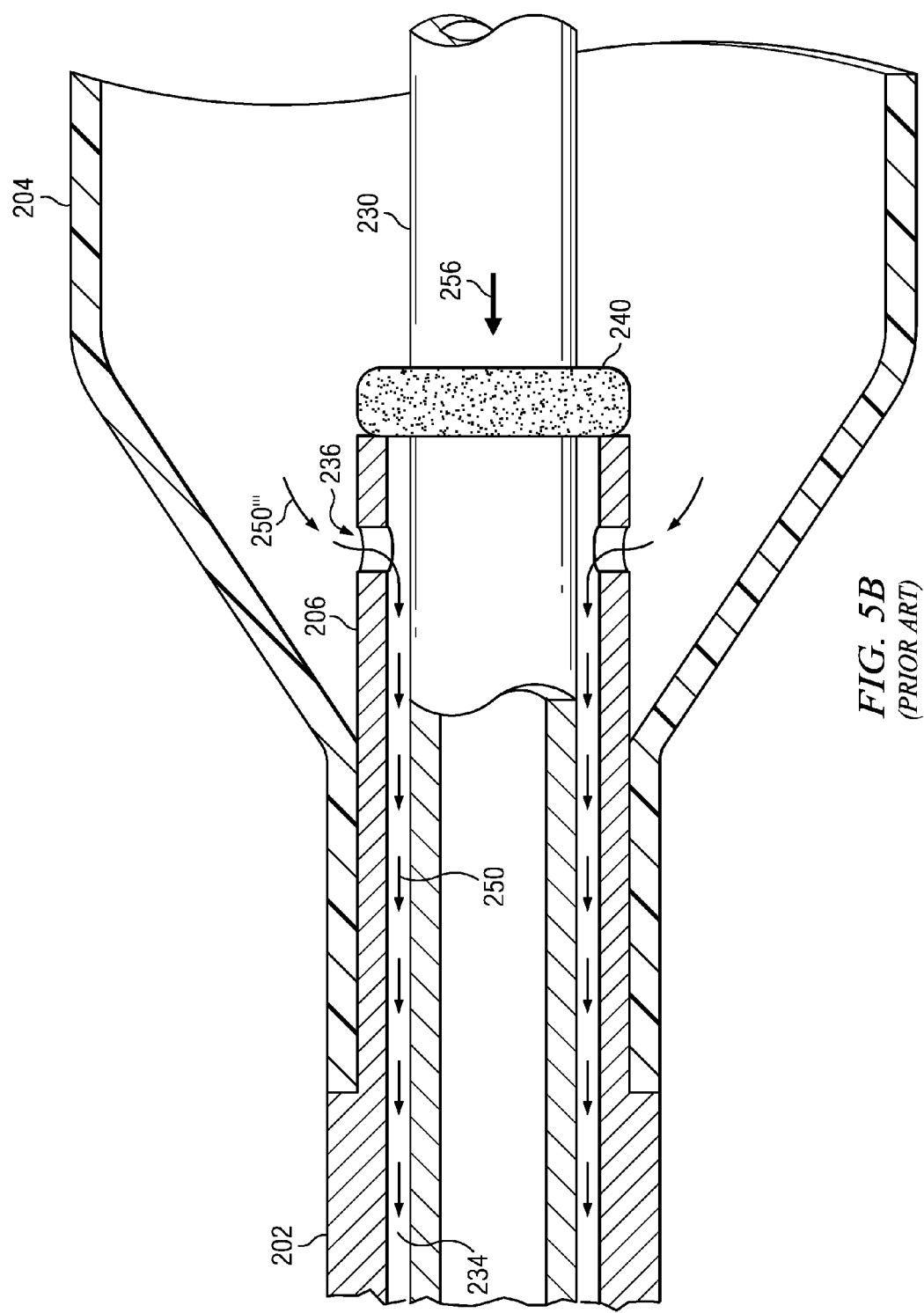

FIG. 5B is an enlarged view of the balloon attachment area of the coaxial catheter shaft 202 during the early stages of deflation of the balloon 204. Deflation begins as pressure is released at the proximal end of the catheter shaft, causing a negative pressure (relative to the pressure in the balloon) in the annular space 234 between the guidewire tubular member 230 and the outer tubular member 206. The negative pressure in the annular space 234 (i.e., higher pressure in the balloon) causes the fluid 250 to reverse direction and flow (represented by arrows 250''') from the interior of the balloon 204 through the radial ports 236 and back down the annular space toward the proximal end of the shaft. The negative pressure in the annular space 234 also urges the annular stop 240 in the proximal direction (represented by arrow 256) against the end of the outer tubular member 206, thus closing any temporary annular passage 254 (FIG. 5A) and preventing the flow of fluid 250 from the interior of the balloon 204 directly into the end of the outer tubular member. In this condition, fluid 250 may only flow from the interior of the balloon 204 into the annular space 234 via the radial ports 236. Because the area of the radial ports 236 is typically small compared to the area of the temporary annular passage 254, deflation of the balloon may proceed more slowly than inflation.

Figure 5C:
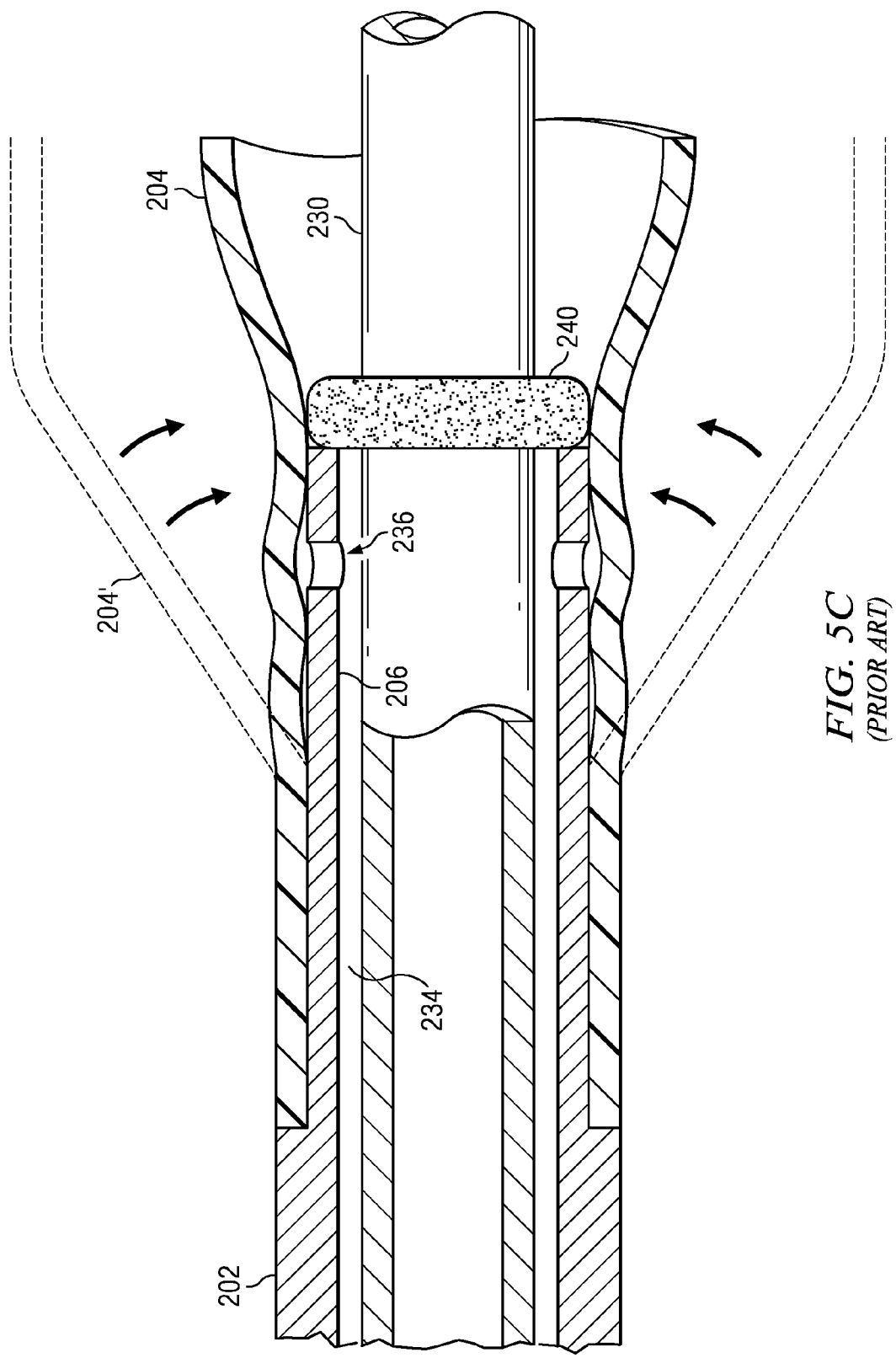

FIG. 5C is an enlarged view of the balloon attachment area of the coaxial catheter shaft 202 during the later stages of deflation. As the inflation fluid 250 is removed from within the balloon 204, the walls of the balloon collapse inward from the fully inflated position (denoted 204') toward the outer tubular member 206 and/or guidewire tubular member 230. When the walls of the balloon fall over the radial ports 236, the negative pressure within the annular space 234 may urge the wall against the port, thereby wholly or partially blocking further fluid flow through the port. As each port 236 becomes covered by the collapsing balloon wall, deflation proceeds more slowly.

FIG. 5D is a partial longitudinal sectional view of the dilation balloon catheter assembly 200 of FIG. 2 in a deflated configuration. As previously described, as dilation balloon 204 is deflated from the configuration illustrated in FIG. 2 to the deflated configuration shown in FIG. 5D, there is a possibility that dilation balloon 204 may cover or obstruct holes 236 as the inflation fluid is removed from the balloon under negative pressure. Such obstruction of holes 236 may result in an increase in the amount of time required to deflate dilation balloon 204 before extraction from a body lumen or movement of the catheter to a new location.

Referring still to FIG. 5D, the prior art configuration of outer tubular member 206, guidewire tubular member 230 and stop member 240 requires that the outer tubular member extend past the proximal neck 214 of dilation balloon 204 and at least into the proximal cone section 220 of the balloon such that the balloon can be inflated and deflated through holes 236. Thus, the diameter of balloon dilation catheter 200 in the deflated state and in the area 242 from the proximal end of neck 214 into proximal cone section 220 of the balloon is determined by the combination of the guidewire tubular member 230, outer tubular member 206 and the wall of proximal cone section 220. Although not shown to scale in the drawings, it should be noted that the wall thickness of proximal cone section 220 tends to be greater than the wall thickness of barrel section 218 since dilation balloon 204 is typically blow-molded from a tube of plastic material originally having a uniform wall thickness along its length. During blow-molding, the barrel walls stretch more than the cone walls, thus leaving the cone areas much thicker than the walls. Consequently, the diameter of balloon dilation catheter 200 in the area 242 may be larger than the adjacent areas of catheter assembly 200, requiring a larger introducer to insert the assembly into a body lumen.

FIG. 6 is a longitudinal section of a catheter assembly 300 including a coaxial shaft according to the disclosure. Catheter assembly 300 includes a coaxial catheter shaft 302 having a proximal end that is affixed to an access fitting 106 (FIG. 1) and a dilation balloon 304 attached to the catheter shaft. Catheter shaft 302 includes an outer tubular member 306 having a proximal end 310 and a distal end 312. Dilation balloon 304 includes proximal and distal neck sections 314, 316, respectively, a barrel section 318 and proximal and distal cone sections 320, 322 disposed between the barrel section and the cone sections. Outer tubular member 306 may include a necked down or reduced diameter section 324 adjacent the distal end 312 of the outer tubular member. The reduced diameter section 324 of outer tubular member 306 is adapted and sized to receive the proximal neck 314 of balloon 304 thereover with the distal end of the neck section abutting or adjacent to the proximal end of the reduced diameter portion of the outer tubular member. The proximal neck section 314 of balloon 304 is fitted over and adhered to the outer tubular member 306 in the reduced diameter section 324 of the member. As illustrated, outer tubular member 306 does not extend into proximal cone section 320 of balloon 304 and terminates within, at or adjacent to the distal end of proximal neck section 314 of balloon 304. Thus, in one embodiment, the distal end 312 of outer tubular member 306 is positioned and located proximal to the proximal end of proximal cone section 320 of balloon 304.

Dilation balloon 304 may be of conventional construction and may be compliant, non-compliant or semi-compliant. Non-compliant balloons are typically formed from a substantially non-elastic material such a non-elastic polyethylene terephthalate (PET) of a non-elastic nylon. Alternatively, a compliant balloon may be formed from an elastomer such as a polyurethane or an elastomeric nylon. Semi-compliant balloons may be formed from PET, nylon, and other thermoplastic materials. For purposes of illustration, balloon 304 is shown in its inflated configuration in FIG. 6. It will be understood that the relative length and diameter of the balloon 304 may vary significantly from that illustrated in FIG. 6.

Referring still to FIG. 6, catheter assembly 300 includes a guidewire tubular member 330 slideably disposed within outer tubular member 306. Guidewire tubular member 330 extends through outer tubular member 306 from access fitting 106 and through dilation balloon 304. The portion of guidewire tubular member 330 extending beyond the distal end of outer tubular member 306 is sized and adapted to pass through the interior of the dilation balloon and to be connected to the distal neck section 316 of balloon 304.

The distal neck section 316 of balloon 304 is adhered to guidewire tubular member 330 such that the balloon is advanced through a body lumen with catheter shaft 302 as the shaft is inserted into the body lumen. The cylindrical inner surface of the outer tubular member 306 and the cylindrical outer surface of the guidewire tubular member 330 define an annular inflation/deflation lumen 334 extending from inflation/deflation port 126 (FIG. 1) and into dilation balloon 304. A fluid, typically an incompressible fluid such as saline solution, may be introduced through inflation/deflation port 126 into annular inflation/deflation lumen 334 to inflate balloon 304. To deflate the balloon, a negative pressure may be applied via inflation/deflation port 126 (FIG. 1) to remove the fluid from balloon 304.

Outer tubular member 306 and/or guidewire tubular member 330 of catheter shaft 302 may be formed of suitable materials such as thermoplastics, elastomers, metals or metal alloys. Different materials may be selected based upon the desired stiffness of catheter shaft 302. In some embodiments, outer tubular member 306 and/or guidewire tubular member 330 of catheter shaft 302 may be formed from a polyimide or a polyamide plastic such as nylon. In some variations, one or both of outer tubular member 306 and guidewire tubular member 330 may be loaded with a material such as bismuth to provide radiopacity.

Dilation balloon 304 may be attached to the distal end of outer tubular member 306 and to the guidewire tubular member 330 using various techniques and configurations known in the art. In one variation, an epoxy adhesive is used to connect the proximal neck section 314 of balloon 304 directly to the exterior surface of the outer tubular member 306 with a fluid tight seal. Similarly, an epoxy adhesive may be used to form a fluid tight seal between the distal neck section 316 of balloon 304 and the outer surface of guidewire tubular member 330. In other embodiments, the connection between proximal neck section 314 of balloon 304 and exterior surface of the outer tubular member 306 and the connection between distal neck section 316 of balloon 304 and guidewire tubular member 330 may be formed by thermal or solvent welding.

In some embodiments, outer tubular member 306 may be sheathed in a jacket (not shown) made of a different material. The jacket may extend partially or along the entire length of tubular member 306. Typically, the jacket is not used to provide additional structural strength, but rather to change certain characteristics of the outer tubular member. For example, a jacket may be made of a material that provides a smooth exterior surface that minimizes the tendency for blood cells to accumulate thereupon and/or of a hydrophilic material that exhibits lubricity when it comes into contact with blood. The jacket may be extruded or co-extruded around the outer tubular member 306 during its manufacture, or it may be bonded to the outer tubular member by thermal-compression molding or similar processes at a later time. In one embodiment, a jacket may be formed of polyether block amide (PEBA) thermoplastic elastomer, such as that sold under the trademark Pebax®. PEBA elastomers such as Pebax® may be readily loaded with radiopacifiers, e.g., bismuth, and are available in plasticizer and additive-free medical grades having nominal hardnesses (Shore D method) ranging from about Shore D 25 to about Shore D 72.

FIG. 7 is a partial cross-sectional view of catheter assembly 300 taken through line 7-7 of FIG. 6. Referring to FIGS. 6 and 7 in conjunction, one or more radial projections, also called legs 336 are formed around the circumference of guidewire tubular member 330 at or adjacent to the proximal end of proximal cone section 320 of balloon 304. As illustrated, legs 336 are located on guidewire tubular member 330 distal from the distal end 312 of outer tubular member 306. Legs 336 extend radially outward from guidewire tubular member 330 such that the distance (denoted by d) of the diameter of a circle drawn around the outermost ends of the legs 336 is greater than the inside diameter of outer tubular member 306. This prevents the legs 336 on the guidewire tubular member 330 from moving into the outer tubular member 306. In one embodiment, legs 336 are disposed at equally spaced circumferential positions around the circumference of guidewire tubular member 330 and extend radially outward therefrom.

Legs 336 collectively serve as a stop, which limits the proximal movement of the guidewire tubular member 330 relative to the outer tubular member 306. Like the annular stop member 240 of the prior art, the legs 336 prevent guidewire tubular member 330 from sliding rearward (i.e., in the proximal direction) within outer tubular member 306 beyond a position where the legs abut the distal end of outer tubular member, thereby preventing balloon 304 from collapsing in an accordion-like manner.

However, unlike the prior art shaft, the legs 336 also define a plurality of fluid passageways 338 between outer tubular member 306, guidewire tubular member 330 and the legs when the legs 336 are abutted against the distal end of outer tubular member 306. Fluid passageways 338 are in fluid communication with annular inflation/deflation lumen 334 such that fluid flowing to or from balloon 304 may pass through passageways 338 as the balloon is inflated or deflated. Simultaneously, legs 336 tend to prevent balloon 304 from collapsing completely over and blocking fluid flow through annual inflation/deflation lumen 334 when the balloon is deflated, especially when the balloon is deflated under negative pressure.

FIG. 8 is a longitudinal sectional view of catheter assembly 300 wherein balloon 304 is in a deflated configuration. As illustrated, legs 336 (FIGS. 6 and 7) tend to prevent balloon 304 from collapsing over annular inflation/deflation lumen 334 and impeding the flow of fluid from the balloon through the annular inflation/deflation lumen during deflation of the balloon. Further, since the proximal end 312 of outer tubular member 306 does not extend into the proximal cone section 320 (FIG. 6) of balloon 304, the proximal cone section of the balloon collapses over the guidewire tubular member 330 and not over the outer tubular member when he balloon is deflated. Thus, the diameter of catheter assembly 300 in the deflated state in the region 342, corresponding to proximal cone section 320 of balloon 304 is determined by the outer diameter of guidewire tubular member 330 and the wall thickness of the balloon in the proximal cone section 320. This is in contrast to the diameter of the equivalent section 242 (FIG. 5) wherein the diameter of the assembly is determined by the diameter of the outer tubular member 206 and the wall thickness of dilation balloon 204. The reduced diameter of assembly 300 in area 342 enables the use of a smaller introducer, facilitating use of assembly 300 in smaller and more tortuous body lumens.

Figures 9A, 9B, 9C, 9D, 9E:
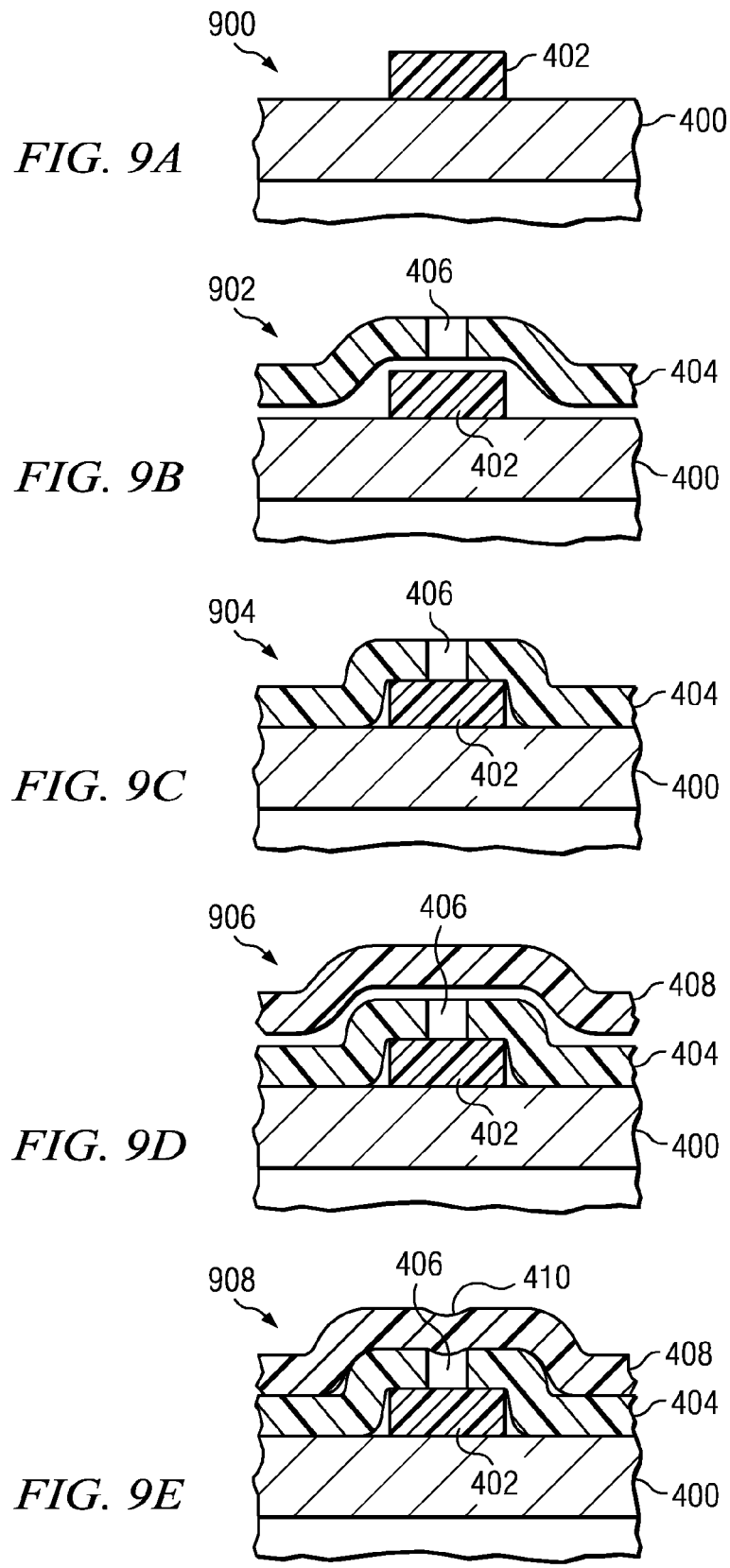
FIGS. 9A-9J illustrate a sequence of steps used in one method of constructing a coaxial catheter shaft according to the disclosure.

FIGS. 9A-9J illustrate a sequence of steps used in one method of constructing a coaxial catheter shaft 302 (FIG. 6). Referring now to FIG. 9A, at step 900, a band 402 of thermoplastic material is applied around the circumference of a guidewire tubular member 400. In one embodiment, the material of band 402 is selected to be compatible with, e.g., thermally weldable, to the material of guidewire tubular member 400. Thus, the materials of guidewire tubular member 400 and band 402 typically have softening temperatures in a range such that the materials will flow together or fuse when heated to a selected temperature.

Referring now to FIG. 9B, at step 902, a first layer of heat shrink material 404 is applied over and circumferentially around band 402 and guidewire tubular member 400. Typically, the thickness of first layer 404 is the same as the length of the legs 336 (FIG. 6) to be formed. Layer 404 of heat shrink material may be in the form of a film, tape or tube and may be a fluoropolymer such as polytetratfluororethylene (PTFE) or other suitable material having the desired properties. First heat shrink layer 404 includes perforations 406 positioned at spaced apart circumferential locations around the perimeter of band 402. In one embodiment, four perforations 406 are formed in first heat shrink layer 404 such that perforations 406 are spaced at intervals of approximately ninety degrees around the circumference of band 402. Perforations 406 may be formed with a die that punches holes in a strip of heat shrink material at predetermined intervals such that perforations 406 are positioned at the desired location around the periphery of band 402 when the strip is wrapped around the band and guidewire tubular member 400.

Referring now to FIG. 9C, at step 904, the first layer 404 of heat shrink material is heated and/or compressed to conform to the geometry of band 402 and the adjacent portions of guidewire tubular member 400.

Referring now to FIG. 9D, at step 906, a second layer of heat shrink material 408 is wrapped over and circumferentially around guidewire tubular member 400, band 402 and first layer 404 of heat shrink material 404. Layers 404 and 408 of heat shrink material may be in the form of a film, tape or tube and may be a polyolefin, a polyvinylchloride, a fluoropolymer such as polytetratfluororethylene (PTFE, e.g., Teflon), fluorinated ethylene propylene (FEP), polyvinylidene fluoride, (PVDF), or other suitable material having the desired heat shrink properties.

Referring now to FIG. 9E, at step 908, the first and second layers of heat shrink material 404, 408 are then heated and/or compressed to conform to the profile of band 402 and the adjacent areas of guidewire tubular member 400. An oven, heated die or external heat source such as a laser, ultrasonic radiation source or heated air supply may be used to heat first and second layers of heat shrink material 404, 408. As illustrated, surface indentations 410 are formed in second layer 408 at the locations of perforations 406 as the second layer of heat shrink material the step 908 sinks into the hole in first layer 404 of heat shrink material.

Figure 9F:
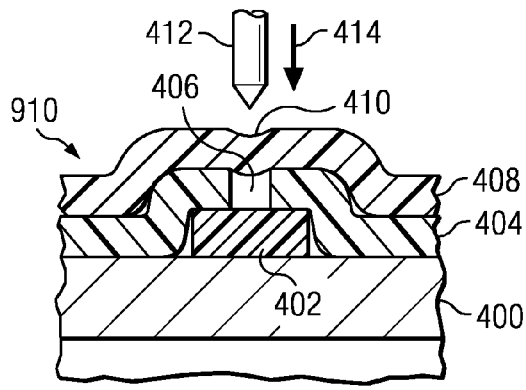

Referring now to FIG. 9F, at step 910, a tool 412 is used to perforate second layer 408 at the location of surface indentations 410 of heat shrink material as indicated by arrow 414. Tool 412 may be an elongate shaft or tube, sharpened at one end to penetrate second layer 408 of heat shrink material. In other embodiments, a laser or heated tool may be used to perforate second layer 408 of the heat shrink material. In one embodiment, indentations 410 are sufficiently deep to visible, with or without magnification, such that the perforation of second layer 408 may be accomplished manually. In other variations, an automated perforating apparatus may be used.

Figure 9G:
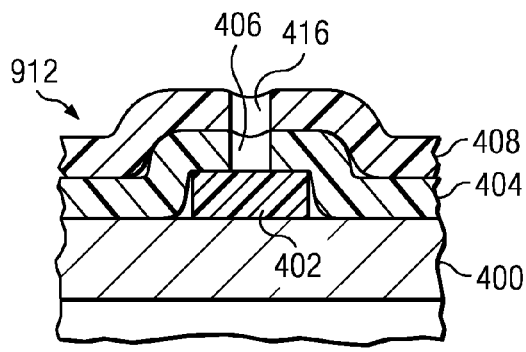

Referring now to FIG. 9G, at step 912, perforations 416 have been formed in second layer 408 of heat shrink material corresponding to the perforations 406 in the first layer 404 of heat shrink material.

Figure 9H:
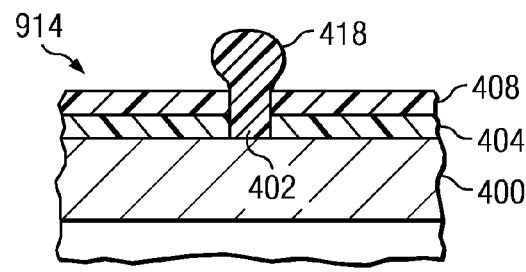

Referring now to FIG. 9H, at step 914, the assembly of first and second heat shrink layers 404, 408, band 402 and guidewire tubular member 400 is then heated and compressed (i.e., by the shrinking action of the heat shrink layers) to thermally weld the material of band 402 to guidewire tubular member 400 and to extrude the excess material of band 402 through perforations 406 and 416. As illustrated, the excess material of band 402 that is extruded through perforations 406 and 416 forms a cap-like protrusion 418 outside the second layer 408 of heat shrink material. It will be appreciated that, if the material of the band 402 and the guidewire tubular member 400 are sufficiently similar, then after thermal welding of the material of band 402 to the guidewire tubular member, the legs 420 (FIG. 9I) will become an integral part of the guidewire tubular member. In other words, the difference of materials illustrated in FIGS. 9I-9J between the legs 420 and the guidewire tubular member 400 will not be visible.

Figure 9I:
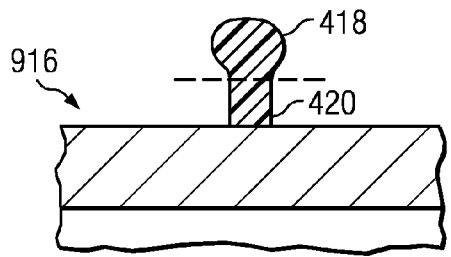

Referring now to FIG. 9I, at step 916, first and second layers 404 and 408 of heat shrink material are removed from guidewire tubular member 400. As illustrated, the material of band 402 has been extruded through perforations 406 and 416 to form legs 420 (corresponding to legs 336 of FIG. 6) with protrusions 418 extending from the legs.

Figure 9J:
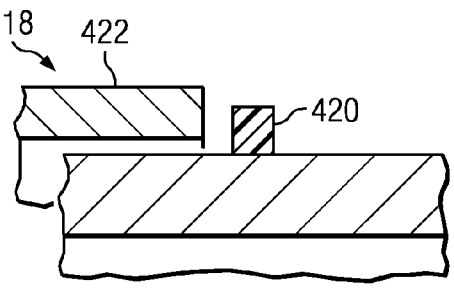

Referring now to FIG. 9J, at step 918, the protrusions 418 are then trimmed (denoted by dotted line), leaving legs 420 at the desired length. In this regard, the width of first layer 404 of heat shrink material is typically selected to correspond the desired length of legs 420. Although the foregoing method utilizes two layers of heat shrink material, it will be appreciated that the method may be modified to use a single layer of heat shrink material or greater than two layers, depending upon the selected materials and specific application. After layers 404 and 408 of heat shrink material have been removed and protrusions 418 trimmed, an outer tubular member 422 may be placed over guidewire tubular member 400 and a dilation balloon installed on the assembly as described above.

In an alternative embodiment, the step 916 previously described in connection with FIG. 9I is replaced by the step (not illustrated) of trimming the cap portions 418 of the extruded band material 402 before one or more of the layers 404 and 408 of heat shrink material are removed. This trimming may be performed by cutting the extruded band material 402 and/or cap protrusion 418 at a level flush with the outer surface of the remaining layers 408 and/or 404 of the heat shrink material. In such case, the legs 420 formed by the trimming will have the thickness of the remaining layers of heat shrink material at the time of trimming. In another alternative embodiment, the trimming may be performed by grinding the extruded band material 402 and/or cap protrusion 418 along with the outer layer of heat shrink material 408. In such case, the legs 420 formed by the trimming will have the thickness of the remaining layer 404 of heat shrink material.

Figure 10:
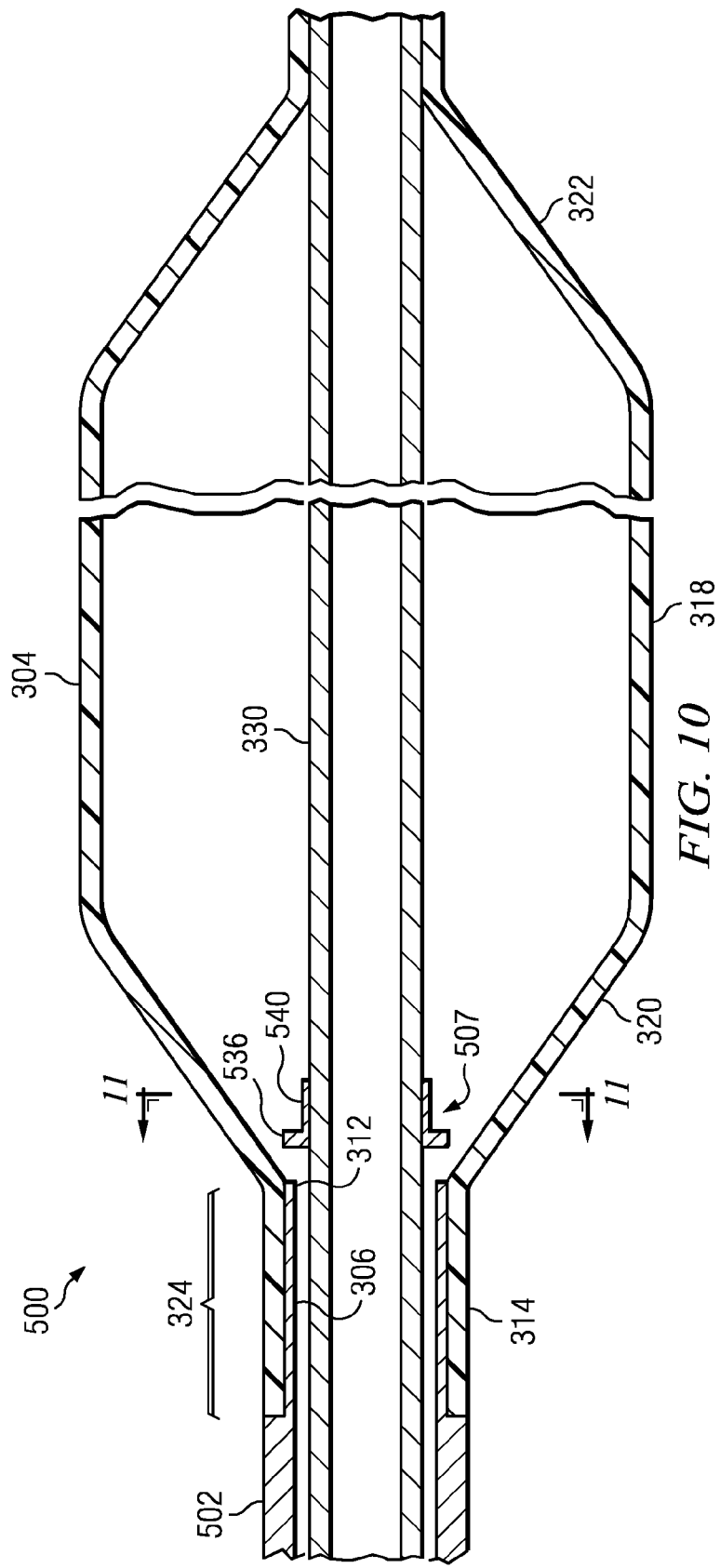
FIG. 10 is a side cross-sectional view of another catheter assembly including a coaxial shaft according to another embodiment.

Referring now to FIGS. 10-13, additional alternative embodiments are illustrated. FIG. 10 is a longitudinal section of a catheter assembly 500 including a coaxial shaft according to the alternative embodiment. Catheter assembly 500 includes a coaxial catheter shaft 502 and a dilation balloon 304 configured substantially as previously described in connection with FIGS. 6-8, except that the shaft 502 comprises a leg assembly 507 including one or more radially projecting legs 536 formed on an annular ring member 540 that is attached to the guidewire tubular member 330. The legs 536 of the leg assembly 507 form a stop, which limits the rearward (i.e., proximal) movement of the guidewire tubular member 330 relative to the outer tubular member 306 as in previous embodiments, thereby preventing balloon 304 from collapsing in an accordion-like manner.

The leg assembly 507 is preferably formed from a polymer material that may be injection molded, for example, a thermoplastic material; however, other polymer and non-polymer materials may be used. The annular ring member 540 of the leg assembly 507 may be attached to the guidewire tubular member 330 using an adhesive, or if the respective materials are compatible with one another, by solvent welding, laser welding, ultrasonic welding, thermal welding or other joining processes.

Referring now also to FIG. 11, there is illustrated a cross-sectional view of catheter assembly 500 taken through line 11-11 of FIG. 10. Referring to FIGS. 10 and 11 in conjunction, it can be seen that the radially projecting legs 536 extend radially outward from leg assembly 507 such that the distance (denoted by d) of the diameter of a circle drawn around the outermost ends of the legs 536 is greater than the inside diameter (denoted by d2 in FIG. 11) of outer tubular member 306. This prevents the legs 536 of the leg assembly 507, and thus also the attached guidewire tubular member 330, from moving too far in the proximal direction into the outer tubular member 306.

Referring still to FIG. 11, the exterior diameter (denoted by d3 in FIGS. 11-12) of the annular ring member 540 of the leg assembly 507 is preferably smaller than the inner diameter d2 of the distal end 312 of the outer tubular member 306. This allows the inflation/deflation fluid to freely move in and out of the balloon 304 through the axial passages 338 between the legs 536, even during the later stages of balloon deflation.

Referring now to FIGS. 12 and 13, there are shown, respectively, a front view and a side cross-sectional view of an exemplary embodiment of the leg assembly 507. In the illustrated example, the leg assembly 507 includes four legs 536 spaced equidistantly around the annular ring member 540. In other embodiments, other numbers of legs 536, e.g., two, three, five, six or more, may be provided, and these legs may be evenly or unevenly spaced around the periphery of the annular ring member 540.

It will be appreciated by those skilled in the art having the benefit of this disclosure that this coaxial catheter shaft having balloon attachment feature with axial fluid path provides a coaxial catheter shaft for a dilation catheter assembly and a dilation catheter assembly with improved characteristics. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A catheter shaft for a balloon dilation catheter to be utilized with a guidewire, the shaft having a proximal end and a distal end, the shaft comprising:
    an outer tubular member having a bore, a proximal end and a distal end;
    a guidewire tubular member coaxially disposed within the bore of the outer tubular member along the length of the outer tubular member wherein an inner surface of the outer tubular member and an outer surface of the guidewire tubular member define an annular inflation/deflation lumen extending between the proximal end of the shaft and the distal end of the outer tubular member; and
    a plurality of legs extending from the guidewire tubular member, at least one of the legs extending radially beyond the inside diameter of the outer tubular member such that the leg blocks movement of the guidewire tubular member into the outer tubular member when the leg of the guidewire tubular member abuts the distal end of the outer tubular member.

2. The catheter shaft for a balloon dilation catheter of claim 1, further comprising a plurality of legs positioned at spaced apart circumferential positions around the exterior perimeter of the guidewire tubular member wherein the legs define a plurality of fluid passageways between the outer tubular member and the guidewire tubular member when the legs are abutted against the distal end of outer tubular member.

3. The catheter shaft for a balloon dilation catheter of claim 1, wherein the legs are disposed at equally spaced circumferential positions around the circumference of the guidewire tubular member and extend radially outward therefrom.

4. The catheter shaft for a balloon dilation catheter of claim 1, wherein the legs are formed from a thermoplastic material.

5. The catheter shaft for a balloon dilation catheter of claim 4, wherein the guidewire tubular member is formed from a thermoplastic material and wherein the legs are affixed to the guidewire tubular member by thermal welding.

6. The catheter shaft for a balloon dilation catheter of claim 1, wherein the outer tubular member includes a reduced diameter distal portion adapted to receive the proximal neck portion of a dilation balloon with the proximal end of the proximal neck portion in abutting relation with the proximal end of the reduced diameter portion of the outer tubular member.

7. The catheter shaft for a balloon dilation catheter of claim 1, wherein the distal end of the outer tubular member is adapted for connection to a proximal neck portion of a dilation balloon, and the portion of the guidewire tubular member extending beyond the distal end of the outer tubular member is adapted to pass through the interior of the dilation balloon and to be connected to the distal end of the balloon.

8. The catheter shaft of claim 1, wherein the proximal end of the shaft is adapted for connection to an access fitting having a first port for conveying a guidewire into the guidewire tubular member and a second port for conveying a fluid into the inflation/deflation lumen.

9. A dilation catheter assembly, the assembly including:
    a catheter shaft having a proximal end and a distal end, the shaft including an outer tubular member having a bore, a proximal end and a distal end, and a guidewire tubular member coaxially disposed within the bore of the outer tubular member along the length of the outer tubular member, an inner surface of the outer tubular member and an outer surface of the guidewire tubular member defining an annular inflation/deflation lumen extending between the proximal end of the shaft and the distal end of the outer tubular member;
    a dilation balloon connected to the distal end of the outer tubular member and to the guidewire tubular member, the dilation balloon including proximal and distal neck sections, a barrel section and proximal and distal cone sections disposed between the proximal and distal neck sections and the barrel section; and
    a plurality of legs extending from the guidewire tubular member distal from the distal end of the outer tubular member, the legs extending radially outward from the guidewire tubular member and beyond the inside diameter of the outer tubular member such that the legs block movement of the guidewire tubular member into the outer tubular member when the legs abut the distal end of the outer tubular member.

10. The dilation catheter assembly of claim 9, wherein the dilation balloon is one of a compliant, semi-compliant or non-compliant balloon.

11. The dilation catheter assembly of claim 9, wherein the legs define a plurality of fluid passageways between the outer tubular member and the guidewire tubular member when the legs are abutted against the distal end of the outer tubular member.

12. The dilation catheter assembly of claim 9, wherein the legs are disposed at equally spaced circumferential positions around the circumference of the guidewire tubular member and extend radially outward therefrom.

13. The dilation catheter assembly of claim 9, wherein the distal end of the outer tubular member is adapted for connection to a proximal neck portion of the dilation balloon, and the portion of the guidewire tubular member extending beyond the distal end of the outer tubular member adapted to pass through the interior of the dilation balloon and to be connected to the distal end of the balloon.

14. The dilation catheter assembly of claim 9, wherein the outer tubular member includes a reduced diameter distal portion adapted to receive the proximal neck portion of the dilation balloon with the proximal end of the proximal neck portion of the balloon in abutting relation with the proximal end of the reduced diameter portion of the outer tubular member.

15. The dilation catheter assembly of claim 9, wherein the distal end of the outer tubular member is positioned proximal to the proximal neck portion of the dilation balloon.

16. The dilation catheter assembly of claim 9, wherein the guidewire tubular member is formed from a thermoplastic material and wherein the legs are affixed to the guidewire tubular member by thermal welding.

17. The dilation catheter assembly of claim 9, wherein the outer tubular member includes a reduced diameter distal portion adapted to receive the proximal neck portion of a dilation balloon with the proximal end of the proximal neck portion in abutting relation with the proximal end of the reduced diameter portion of the outer tubular member.

18. The dilation catheter assembly of claim 17, wherein the distal end of the outer tubular member is affixed to the proximal end of the dilation balloon with an adhesive.

19. The dilation catheter assembly of claim 9, wherein the proximal end of the shaft is adapted for connection to an access fitting having a first port for conveying a guidewire into the guidewire tubular member and a second port for conveying a fluid into the inflation/deflation lumen.

20. The dilation catheter assembly of claim 9, further comprising an access fitting affixed to the proximal end of the shaft, the access fitting including a first port allowing guidewire to pass into and out of the guidewire tubular member, and a second, inflation/deflation port in fluid communication with the annular inflation/deflation lumens.

* * * * *